United States Patent [19]

Clavell, Jr.

[11] Patent Number: 5,595,635
[45] Date of Patent: Jan. 21, 1997

[54] APPARATUS FOR MEASURING LEAD CONTENT OF WATER

[75] Inventor: Cesar Clavell, Jr., San Diego, Calif.

[73] Assignee: The United States of America as represented by the Secretary of the Navy, Washington, D.C.

[21] Appl. No.: 525,451

[22] Filed: Sep. 8, 1995

[51] Int. Cl.⁶ ................................................. G01N 27/26
[52] U.S. Cl. ........................ 204/412; 204/406; 204/407; 205/775; 205/789.5
[58] Field of Search ...................... 204/412, 434, 204/406, 407; 205/775, 789, 789.5

[56] References Cited

U.S. PATENT DOCUMENTS

| | | | |
|---|---|---|---|
| 2,928,782 | 3/1960 | Leisey | 204/405 |
| 3,629,089 | 12/1971 | Luck | 204/412 |
| 4,146,436 | 3/1979 | Kellerman et al. | 204/434 |
| 4,452,682 | 6/1984 | Takata et al. | 204/415 |
| 4,581,122 | 4/1986 | Hammond et al. | 204/412 |
| 4,707,230 | 11/1987 | Ajami . | |
| 4,744,870 | 5/1988 | Kauffman . | |
| 4,764,258 | 8/1988 | Kauffman . | |
| 4,775,450 | 10/1988 | Ajami . | |
| 4,839,017 | 6/1989 | Taniguchi et al. . | |
| 5,100,530 | 3/1992 | Dorr et al. | 204/412 |
| 5,125,894 | 6/1992 | Phipps et al. . | |
| 5,217,594 | 6/1993 | Henkens et al. . | |
| 5,217,595 | 6/1993 | Smith et al. | 204/412 |
| 5,250,171 | 10/1993 | Warburton et al. | 204/412 |
| 5,284,566 | 2/1994 | Cuomo et al. | 204/431 |
| 5,286,364 | 2/1994 | Yacynych et al. . | |
| 5,288,374 | 2/1994 | Watanabe et al. | 204/412 |
| 5,310,687 | 5/1994 | Bard et al. . | |
| 5,364,568 | 11/1994 | Pope et al. . | |
| 5,368,707 | 11/1994 | Henkens et al. . | |
| 5,376,244 | 12/1994 | Preidel . | |
| 5,437,772 | 8/1995 | De Castro et al. | 204/434 |

OTHER PUBLICATIONS

D. Jagner, "Instrumental Approach to Potentiometric Stripping Analysis of Some Heavy Metals", *Analytical Chemistry*, vol. 50, No. 13, Nov. 1978, pp. 1924–1929.

J. Wang et al., "Mercury–Free Disposable Lead Sensors Based on Potentiometric Stripping Analysis at Gold–Coated Screen–Printed Electrodes", *Analytical Chemistry*, vol. 65, No. 11, 1 Jun. 1995, pp. 1529–1532.

*Primary Examiner*—T. Tung
*Attorney, Agent, or Firm*—Harvey Fendelman; Michael A. Kagan; Eric James Whitesell

[57] ABSTRACT

An electrochemical cell for measuring concentrations of metal ions comprises a sampling enclosure including a working electrode, a reference electrode, and a counter electrode. Ports are provided in the sampling enclosure for the introduction and removal of a liquid sample, an auxiliary reagent, and a standard solution. A stirring mechanism maintains a uniform composition of the liquid sample during operation of the cell. The electrochemical cell is operated by introducing the liquid sample into the sampling enclosure, applying a plating voltage between the working electrode and the counter electrode, and measuring the voltage response of the working electrode when the applied voltage is removed. The concentration of metal ions is then calculated from the voltage response. A standard solution is added to the liquid sample, after which the measurement is repeated to calculate the concentration of metal ions relative to the standard solution.

12 Claims, 3 Drawing Sheets

1

APPARATUS FOR MEASURING LEAD CONTENT OF WATER

BACKGROUND OF THE INVENTION

The present invention relates to a method and apparatus for detecting minute quantities of trace metals in water. More specifically, but without limitation thereto, the present invention relates to measuring lead concentration in water with a stopped flow electrochemical cell.

Heavy metals such as lead have received increasing recognition as serious threats to the environment and to human health. The effects of lead may not be acute, thus chronic toxicity is of particular concern because the metal accumulates in tissues over a period of long-term exposure. This may lead to mental and physical abnormalities, especially in children.

The detrimental effects of lead in the environment have long been recognized. Lead poisoning has been detected in waterfowl due to lead shot. The elimination of tetraethyl lead as an octane booster in gasoline was part of an effort to prevent this metal from further contaminating soil and water sources. However, the use of lead in glazes, paints, and coatings, for example, has occurred over long periods of time, and lead in pottery may have contributed to the demise of earlier civilizations.

As a result of past long-term use of lead in a wide range of products, it is difficult to avoid exposure to this element. Lead-solder joints in water pipes, for example, contribute to the lead content of drinking water. Modern interior paints are lead-free, but in older homes there may significant exposure to lead from older lead-based paints, even when such paint layers have been painted over with the newer lead-free paints. This practice has created a risk of lead toxicity for those groups most susceptible to lead poisoning, especially children.

The long-term effect of lead on the health of children is significant. This is of concern to parents as well as to health care professionals and the federal government. Programs being developed to detect the presence of harmful substances in the environment will undoubtedly encourage the discovery of rapid, reliable methods for detecting low levels of lead.

Instruments currently available for monitoring trace metals generally require highly trained personnel to perform relatively sophisticated techniques. Consequently, such analyses are performed in centralized laboratories set up for routine multiple analysis. There is a need, however, for instrumentation available for use in the field or even in homes, hospitals, and commercial housing that is portable and operable without requiring highly trained technical personnel.

SUMMARY OF THE INVENTION

The lead analyzer of the present invention addresses the problems described above, and may provide further related advantages. The following description of a method and apparatus for analyzing lead content of water does not preclude other embodiments and advantages of the present invention that may exist or become obvious to skilled artisans.

An electrochemical cell of the present invention for measuring concentrations of metal ions comprises a sampling enclosure including a working electrode, a reference electrode, and a counter electrode. Ports are provided in the sampling enclosure for the introduction and removal of a liquid sample, an auxiliary reagent, and a standard solution. A stirring mechanism maintains a uniform composition of the liquid sample during operation of the cell.

The electrochemical cell is operated by introducing the liquid sample into the sampling enclosure, applying a plating voltage between the working electrode and the counter electrode, and measuring the voltage response of the working electrode when the applied voltage is removed. The concentration of metal ions is then calculated from the voltage response. A standard solution is added to the liquid sample, after which the measurement is repeated to calculate the concentration of metal ions relative to the standard solution.

The features and advantages summarized above in addition to other aspects of the present invention will become more apparent from the description, presented in conjunction with the following drawings.

DESCRIPTION OF THE INVENTION

The following description is presented solely for the purpose of disclosing how the present invention may be made and used. The scope of the invention is defined by the claims.

Figure 1:
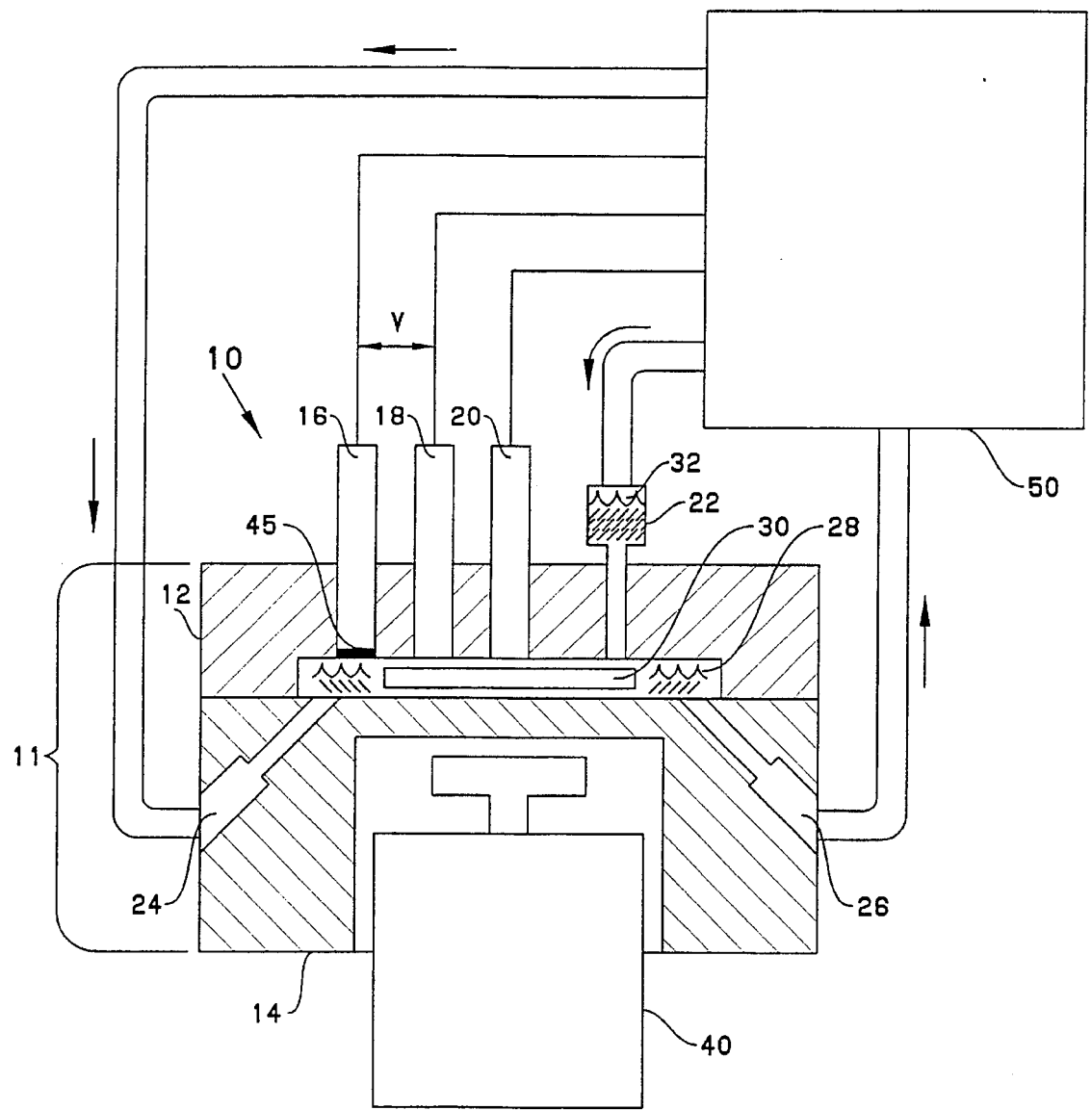
FIG. 1 is a cross-sectional view of the stopped flow electrochemical cell of the present invention.

Referring to FIG. 1, an electrochemical cell 10 comprises a sampling enclosure 11 divided into an upper portion 12 and a lower portion 14. Upper portion 12 and lower portion 14 may be made of acrylic plastic or other materials that may readily be machined and do not leach metal ions. Suitable materials for making sampling enclosure 11 include plexiglass, polypropylene, "TEFLON", "PEEK", and "KEL-F". Upper portion 12 has ports for a working electrode 16, a counter electrode 18, and a reference electrode 20. An additional reagent input port 22 may be provided for the introduction of an auxiliary reagent 32 into sampling enclosure 11. Sampling enclosure 11 has a filling port 24 and an emptying port 26 for conducting a liquid sample 28. A stirring bar 30 inside enclosure 11 ensures that the composition of liquid sample 28 remains uniform during the operation of the cell. Stirring bar 30 may be driven by a magnetically coupled drive motor 40, thus eliminating the need for drive shaft seals and the possibility of contaminating liquid sample 28 through the seals.

After sampling enclosure 11 has received liquid sample 28 through filling port 24, auxiliary reagent 32 may be added through reagent input port 22 while liquid sample 28 is agitated by stirring bar 30. The composition of auxiliary reagent 32 depends on the metals being analyzed. For analyzing lead, copper, cadmium, and zinc, auxiliary agent 32 may comprise a combination of two reagents. The first reagent is a matrix of mercury, citrate (preferably about 0.01 Molars) and hydrochloric acid. The mercury replenishes a thin mercury film 45 on working electrode 16 for each analysis cycle. The hydrochloric acid adjusts the acidity of the sample to about pH 2.5. The second reagent is a standard solution containing a known concentrate of each metal to be analyzed.

During an analysis cycle, a voltage V is applied between working electrode 16 and counter electrode 18 to cause metallic ions to be reduced and amalgamate with mercury film 45 on working electrode 16. Voltage V is then removed and the open circuit voltage response between working electrode 16 and reference electrode 20 is measured while the open circuit voltage returns to a resting potential. As the open circuit voltage returns to the resting potential, metal ions on working electrode 16 are oxidized and return to solution in liquid sample 28 at a voltage characteristic of each metal.

Figure 2:
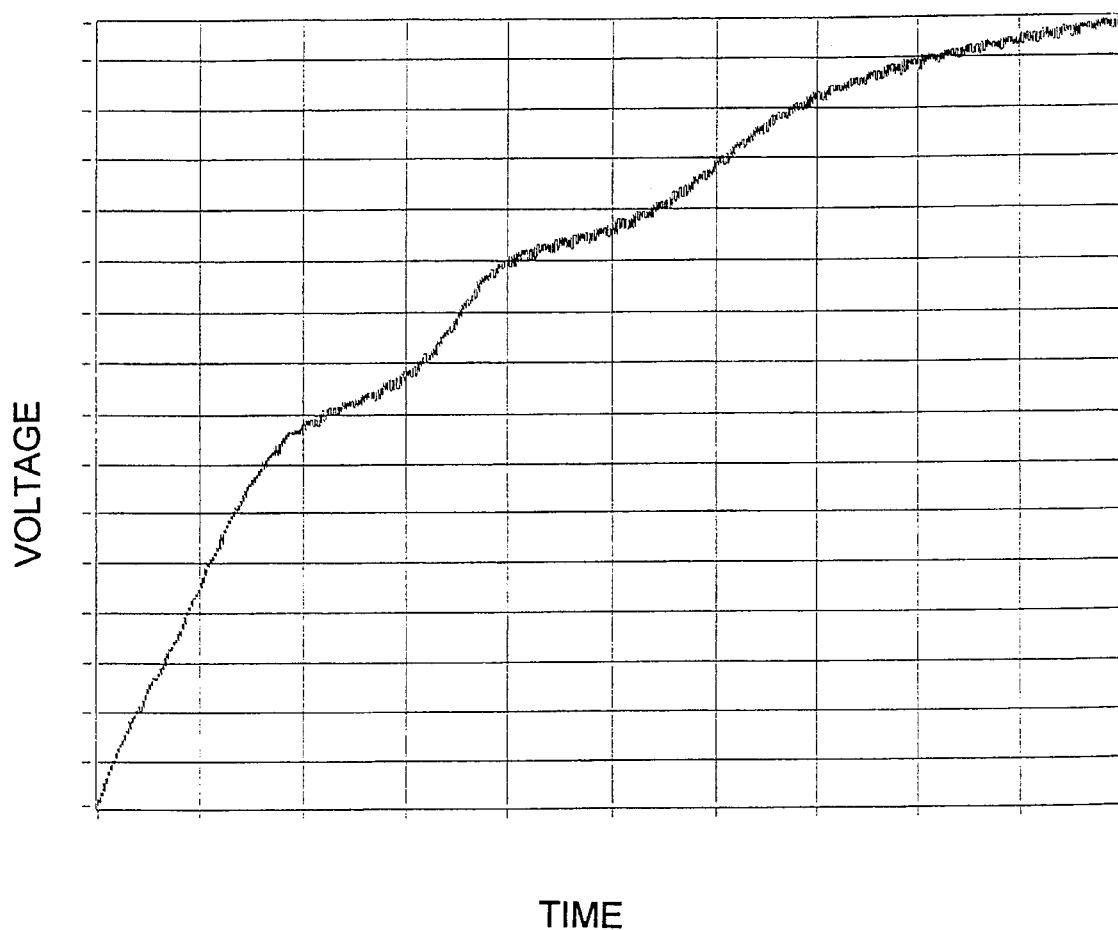
FIG. 2 is an exemplary graph of the open circuit voltage response of the electrochemical cell.

FIG. 2 is an example of the open circuit voltage response of electrochemical cell 10. The voltage response appears as a stepped curve when plotted over time. The time between steps is generally proportional to the concentration of metals in liquid sample 28.

Figure 3:
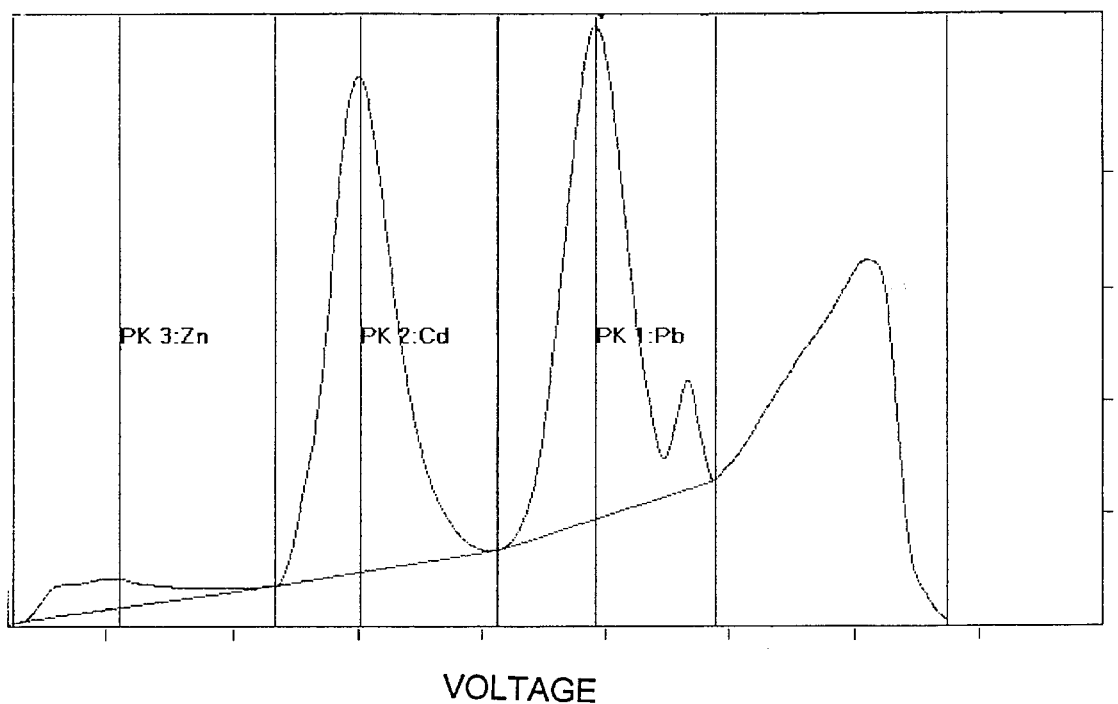
FIG. 3 is an exemplary graph of the open circuit voltage response mapped into voltage bins for a liquid sample containing zinc, cadmium, and lead.

Mapping the voltage response of FIG. 2 into voltage bins results in the plot of FIG. 3. The peaks are representative of the metal ion concentrations in liquid sample 28. In this example, concentrations of zinc, cadmium, and lead are shown. The area under each peak is proportional to the concentration of the corresponding metal in the sample. These peaks are centered at approximately −0.2 V for copper, −0.4 V for lead, −0.65 V for cadmium, and −1 V for zinc.

After the open circuit voltage has decayed to the resting potential, the standard solution portion of auxiliary reagents 32 is added to liquid sample 28, and the analysis cycle described above is repeated. The ratio of the corresponding areas under the voltage peaks corresponds to the original concentration of metal ions in liquid sample 28. Liquid sample 28 is then drained from the cell through emptying port 26 and a new liquid sample 28 is received into enclosure 11 through filling port 24.

For a plating time of about 40 seconds, a complete sample cycle including the addition of the standard solution and voltage analyses requires about three minutes. The measurement of the voltage response may be completed in approximately 100–200 milliseconds.

Working electrode 16, reference electrode 20, and counter electrode 18 are available commercially, for example, from Bioanalytical Systems. Working electrode 16 is typically made of glassy carbon (although bare gold and carbon may also be used), reference electrode 20 is typically made of silver/silver chloride, and counter electrode 18 is typically made of platinum. A working voltage of about −1 V is typically used in a measurement for lead content.

Electrochemical cell 10 may readily be connected to an automated instrument system 50 comprising a voltage source for applying a voltage to counter electrode 18, a voltage meter for measuring the open circuit voltage of reference electrode 20, a calculator for displaying the concentration of metal ions, a reagent valve for adding reagent 32 via reagent input port 22, and control valves and for filling and emptying electrochemical cell 10 via filling port 24 and emptying port 26, respectively. Automated instrument system 50 may be made according to well-known techniques to perform unattended measurements at selected intervals, thus facilitating research and monitoring in the field, including home and commercial water supplies.

The dimensions of electrochemical cell 10 are preferably chosen to accommodate standard electrodes in proper alignment with lower portion 14 without requiring disassembly of upper portion 12 from lower portion 14. The volume of liquid sample 28 is preferably the minimum possible consistent with the use of standard electrodes, i.e., approximately three milliliters. Using the minimum possible volume is important for conserving the sample, for making the instrument as compact as possible for ease of portability, and for reducing the amount of hazardous waste produced by mercury film 45.

Reagent input port 22 allows precise delivery of standard reagent solutions into electrochemical cell 10 to ensure accurate analysis of liquid sample 28. Homogeneity of liquid sample 28 is maintained by stirring bar 30. Stirring bar 30 may be driven by a magnetically coupled drive motor 40, thus eliminating the need for drive shaft seals and the possibility of contaminating liquid sample 28 through the seals.

Other modifications, variations, and applications of the present invention may be made in accordance with the above teachings other than as specifically described to practice the invention within the scope of the following claims.

What is claimed is:

1. An electrochemical cell for measuring concentration of metal ions in a liquid sample, comprising:

a sampling enclosure for containing said liquid sample;

a working electrode operably coupled to said sampling enclosure and said liquid sample;

a counter electrode electrically insulated from said working electrode, operably coupled to said sampling enclosure and said liquid sample;

a reference electrode electrically insulated from said working electrode and said counter electrode, operably coupled to said sampling enclosure and said liquid sample;

a voltage meter operably coupled to said working electrode and said reference electrode for measuring an open circuit voltage response; and a calculator operably coupled to said voltage meter for displaying said concentration of said metal ions in said liquid sample as a plot having a peak representative of said concentration of said metal ions calculated by mapping said open circuit voltage response into voltage bins.

2. The electrochemical cell of claim 1, further comprising a filling port operably coupled to said sampling enclosure for introducing said liquid sample into said sampling enclosure.

3. The electrochemical cell of claim 1, further comprising an emptying port operably coupled to said sampling enclosure for removing said liquid sample from said sampling enclosure.

4. The electrochemical cell of claim 1, further comprising a reagent input port operably coupled to said sampling enclosure for introducing a reagent into said liquid sample.

5. The electrochemical cell of claim 1, further comprising a stirring bar operably coupled to said sampling enclosure and said liquid sample.

6. The electrochemical cell of claim 5, further comprising a motor operably coupled to said stirring bar and said sampling enclosure.

7. The electrochemical cell of claim 1, wherein said working electrode comprises a mercury film on one of glassy carbon, bare gold, and bare carbon.

8. The electrochemical cell of claim 1, wherein said reference electrode comprises silver/silver chloride.

9. The electrochemical cell of claim 1, wherein said counter electrode comprises platinum.

10. The electrochemical cell of claim 1, wherein a portion of said sampling enclosure comprises one of acrylic plastic and polypropylene.

11. The electrochemical cell of claim 1, further comprising an automated controller for operating said electrochemical cell, said automated controller including valves for filling said sampling enclosure with said liquid sample, introducing a reagent into said liquid sample, and removing said liquid sample, wherein said automated controller further comprises a a plating voltage source operably coupled to said working electrode and said counter electrode.

12. The electrochemical cell of claim 1, further comprising a display operably coupled to said calculator for displaying a calculated value of said concentration of metal ions.

* * * * *